US008027505B2

(12) United States Patent
Edgar et al.

(10) Patent No.: US 8,027,505 B2
(45) Date of Patent: Sep. 27, 2011

(54) SYSTEM AND METHOD FOR PROVIDING SIMULATED IMAGES THROUGH COSMETIC MONITORING

(75) Inventors: Albert D. Edgar, Austin, TX (US); David C. Iglehart, Austin, TX (US); Rick B Yeager, Austin, TX (US)

(73) Assignee: TCMS Transparent Beauty LLC, Austin, TX (US)

( * ) Notice: Subject to any disclaimer, the term of this patent is extended or adjusted under 35 U.S.C. 154(b) by 899 days.

(21) Appl. No.: 12/028,836

(22) Filed: Feb. 11, 2008

(65) Prior Publication Data

US 2008/0219528 A1 Sep. 11, 2008

Related U.S. Application Data

(60) Provisional application No. 60/889,292, filed on Feb. 11, 2007, provisional application No. 60/889,290, filed on Feb. 11, 2007, provisional application No. 60/889,289, filed on Feb. 11, 2007.

(51) Int. Cl.

| | |
|---|---|
| ***G06K 9/00*** | (2006.01) |
| *A61B 5/00* | (2006.01) |
| *B41J 2/01* | (2006.01) |
| *G09B 19/00* | (2006.01) |

(52) U.S. Cl. ............ 382/100; 600/310; 347/1; 434/100

(58) Field of Classification Search .................. 382/100, 382/128; 600/247, 306, 310, 443, 476, 556, 600/557; 604/112, 137, 289; 347/1; 362/247; 401/119; 434/100

See application file for complete search history.

(56) References Cited

U.S. PATENT DOCUMENTS 5,836,872 A * 11/1998 Kenet et al. .................. 600/306
6,554,452 B1 * 4/2003 Bourn et al. .................. 362/247
2004/0078278 A1 4/2004 Dauga et al.

FOREIGN PATENT DOCUMENTS

WO WO2007022095 A1 2/2007

OTHER PUBLICATIONS

International Search Report for Application No. PCT/US2008/053528, dated Nov. 13, 2008, 5 pages.
International Preliminary Report on Patentability and Written Opinion of the International Searching Authority for Application No. PCT/US2008/053528, dated Aug. 11, 2009, 9 pages.
Notification of First Office Action for Application No. 200880009579.0, dated Jul. 14, 2010, 10 pages.
European Patent Office Action for Application No. 08 729 481.5, dated Aug. 23, 2010, 5 pages.

* cited by examiner

*Primary Examiner* — Abolfazl Tabatabai
(74) *Attorney, Agent, or Firm* — Fish & Richardson P.C.

(57) ABSTRACT

An automated cosmetic applicator uses wide-angle cameras, a high-resolution camera, and a differential lighting process to capture images of a body. Software analyzes these images to identify large and small features of the subject and to use these features as landmarks to create in computer memory a corresponding map that is highly accurate and data rich with pixel-level data about the subject's color, light value and texture characteristics. The rich images may be used for tracking the device on the skin, for making accurate corrections to skin, for simulating possible cosmetic enhancements and selecting a desired correction, and for use in other applications such as video games and animations.

17 Claims, 6 Drawing Sheets

SYSTEM AND METHOD FOR PROVIDING SIMULATED IMAGES THROUGH COSMETIC MONITORING

CROSS-REFERENCE TO RELATED APPLICATIONS

This patent application is related to U.S. Provisional Patent Application No. 60/889,292 filed Feb. 11, 2007 by the present inventors for "SYSTEM AND METHOD FOR PROVIDING SIMULATED IMAGES THROUGH COSMETIC MONITORING" and claims the filing date of that Provisional application; and is related to U.S. Provisional Patent Application No. 60/889,290 filed Feb. 11, 2007 by the present inventors for "HANDHELD APPARATUS, DISPLAY, AND SOFTWARE-BASED POSITIONING FOR THE AUTOMATED APPLICATION OF COSMETICS AND OTHER SUBSTANCES"; and is related to U.S. Provisional Patent Application No. 60/889,289 filed Feb. 11, 2007 by the present inventors for "SYSTEM AND METHOD FOR THE PRECISION WHOLE-BODY APPLICATION OF COSMETICS."

This patent application incorporates by reference the specification, drawings, and claims of U.S. patent application Ser. No. 11/503,806 filed Aug. 14, 2006 by the present inventors for "SYSTEM AND METHOD FOR APPLYING A REFLECTANCE MODIFYING AGENT TO IMPROVE THE VISUAL ATTRACTIVENESS OF HUMAN SKIN"; and copending U.S. patent application Ser. No. 12/028,835 filed Feb. 11, 2008 for "HANDHELD APPARATUS AND METHOD FOR THE AUTOMATED APPLICATION OF COSMETICS AND OTHER SUBSTANCES".

FIELD OF THE INVENTION

The current invention relates to automated computer-controlled methods to obtain digital images and to selectively and precisely apply one or more reflectance modifying agent, such as a dye or pigment, to human skin to improve its visual attractiveness.

BACKGROUND OF THE INVENTION

Prior Cosmetic Techniques and Their Disadvantages

Prior art techniques for modifying the appearance of skin include natural tanning, artificial tanning, and the deliberate application of cosmetics. Each of these prior art techniques has limitations.

Typically, the applications of cosmetic substances to skin are largely manual, for example through the use of brushes, application tubes, pencils, pads, and fingers. The application methods make prior art cosmetics imprecise, labor intensive, expensive, and sometimes harmful, when compared to the computerized techniques of the present invention.

Most prior art cosmetic approaches are based on the application of opaque substances. There is a need for the precise application of reflectance modifying agents (RMAs), such as transparent dyes, to provide a more effective modification of appearance.

Manual cosmetic applications are imprecise compared to computer-controlled techniques, and this imprecision may make them less effective. For example, the heavy application of a foundation base for makeup may cause an unattractive, caked-on appearance. Manual techniques also typically take a long time to employ, as can be seen in any morning commute on a highway, where people frantically take advantage of stops to finish applying their makeup. In addition, manually applied makeup is not cheap, and when the help of professionals such as beauticians is required, is even more expensive. Moreover, often the materials applied to the skin in manual techniques are themselves potentially harmful. For example, a foundation base for makeup may cause skin to dry out and may inhibit the skin's breathing. Sunlight or artificial light used for tanning may cause cancer.

Therefore, there is a need for the precise application of reflectance modifying agents (RMAs) to provide a more effective, more automated, faster, less expensive, and less dangerous modification of the appearance of skin. The cross-referenced U.S. patent application cited above presents a system and method for this need.

In this specification, the terms "reflectance modifying agent" or "RMA" refer to any compound useful for altering the reflectance of another material. Some examples of RMA are inks, dyes, pigments, bleaching agents, chemically altering agents, and other substances that can alter the reflectance of human skin and other features. The terms "dye" and "transparent dyes" are used for brevity in this specification to represent any RMA.

Consumers of cosmetics also need effective techniques that allow them to select desired cosmetic enhancements, such as different shades of makeup, to visualize how those enhancements will look on them, for example on computer displays, and to precisely apply cosmetics onto them to make the selected enhancements. Websites such as MaryKay.com offer virtual makeovers that allow users to try out on their home computer displays different makeup patterns on digital images of different types of women and even on digital images of the users themselves that users submit. However, the images used in virtual makeovers do not provide adequate details for the calculation of advanced RMA enhancements. Nor do they allow users to automatically apply to themselves the cosmetic enhancements that have selected digitally on computer displays. There is a need for a method that lets users employ an RMA applicator and a computer display to view sufficiently detailed digital images of themselves so that they can make virtual cosmetic enhancements to those images and so that they can automatically and precisely apply RMA to themselves to achieve those enhancements.

Consumers also need effective techniques that allow them to make cosmetic enhancements not just to a single area, such as a facial blemish, but over their whole bodies. For example, some people get natural or artificial tans to make their skin look smoother and thus more attractive over their whole bodies. Consumers in East Asia often use cosmetics to make much of their skin look lighter. Consumers also may want to make complex cosmetic enhancements, involving color and texture, to hide defects and enhance their appearance over their whole bodies. Manual techniques to make such whole body cosmetic enhancements can be particularly laborious, time-consuming, and expensive. There is a need for a system and method that lets users make automatic cosmetic enhancements to their whole bodies.

Simulated Digital Images

In this patent application, a "simulated image" refers to a digital image that simulates a real object and can be displayed on a computerized device. A simulation of a real object is a portrayal of the object in any desired manner not strictly limited to aspects revealed by photographic or video data captured about the object. A simulated image can represent a still image of the object or a video clip of the object in motion and may be three dimensional (3D). For example, simulated images are widely used for display on computer screens, cell phones, video games, in animated sections of movies, and in medical imaging.

In general, consumers want to display very realistic simulated images in different media. Moreover, they may want simulated images that represent subjects that they choose. For example, these subjects may be the consumers themselves, their friends, their family members, or their favorite personalities such as movie stars. For instance, a boy may want to put his own face on a 3D action figure in a video game. A woman may want to display a simulated 3D image of her face and head on a computer device and make cosmetic enhancements to that image, so that she can try out different cosmetic effects and hairstyles virtually.

In addition, consumers may want simulated images that are enhanced to be more desirable in some way. For example, a person may want his or her own face to be displayed in a way that makes him or her appear younger and more attractive.

Prior Techniques and Their Disadvantages

Simulated images have been created in a number of ways. They can be drawn by hand and then scanned, photographed, or video recorded and can be created through computer graphics programs, both of which are laborious techniques requiring special skills.

In addition, simulated images can be created by using sensors attached at various points to a real subject, digitally recording the motions the subject, often through multiple cameras, and using computer graphics programs to create simulated characters whose movements and facial expressions are based on those of the recorded subject. In this way, an animation of a cartoon character dancing or smiling may be based on a real actor's movements and expression.

The computer graphics programs used in these processes are increasingly able to transform recorded data about real objects into simulated images. An example is Optasia™, the model-based feature-recognition platform developed by Image Metrics, PLC. The "Technical White Paper" on the Image Metrics Website states that "The Optasia engine can perform rapid model-to-image matching regardless of the model type, including those with high-frequency elements such as texture." Optasia is available on a variety of platforms as a three-layered architecture. All systems use 1) the Optasia core, with 2) a sector specific API (e.g. medical image analysis). Prior knowledge is incorporated in the 3) 'expert' layer (or model).

However, such prior techniques have disadvantages:

- They are all labor intensive and require special skills and special, often cumbersome equipment not readily available to many consumers.
- The simulated images they produce have limited details so that they do not look as realistic as consumers want. Instead, they tend to look artificially smoothed, often because their computer graphics programs must fill in large areas of simulated images with what essentially amounts to guesses and averages as a result of limited collection of data about the subject. These guesses and averages may require complicated algorithms and large amounts of computing power. For example, the three-layered approach of Optasia, mentioned above, is complicated and computing intensive.
- They are difficult for consumers themselves to use to simulate favorite images.
- They are difficult for consumers to use to enhance simulated images in desirable ways.
- Moreover, they are not readily available to many consumers, who may not have access to expensive modeling and graphics software and equipment.

Therefore, there is a need for an automated cosmetic monitoring and enhancement system that can be readily available to consumers, is easy to use, and provides high-resolution realistic image files with rich data about real subjects that can be used for creating simulated images.

BRIEF SUMMARY OF THE INVENTION

These and other needs are addressed by the present invention. The following explanation describes the present invention by way of example and not by way of limitation.

It is an aspect of the present invention to provide high-resolution realistic image files with rich data about real subjects that can be used for creating simulated images.

It is an aspect of the present invention to provide at least one wide-angle camera mounted on an RMA applicator to capture images of a surface such as the human body.

It is another aspect of the present invention to provide a software method to use images captured by at least one wide-angle camera mounted on an RMA applicator to identify large features on a surface such as the human body.

It is another aspect of the present invention to provide a software method to use images captured by at least one high resolution camera mounted on the applicator head on an RMA applicator to identify small features on a surface such as the human body.

It is still another aspect of the present invention to provide a software method to use large and small features identified from captured images to create a map in computer memory of a surface such as the human body.

It is another aspect of the present invention to provide a software method to use a map in computer memory to track the location of an RMA applicator relative to an area of a surface such as the human body.

It is still another aspect of the present invention to provide at least one accelerometer mounted on an RMA applicator to identify changes in the acceleration of the applicator.

It is another aspect of the present invention to provide a software method to use images captured by at least one wide-angle camera mounted on an RMA applicator and data collected by an accelerometer mounted on the applicator to identify large features on a surface such as the human body.

It is another aspect of the present invention to provide a software method to use images captured by at least one high resolution camera mounted on the applicator head on an RMA applicator and data collected by an accelerometer mounted on the applicator to identify small features on a surface such as the human body.

It is another aspect of the present invention to provide a software method to use a map in computer memory and data collected by an accelerometer mounted on an RMA applicator to track the location of an applicator relative to an area of a surface such as the human body.

It is aspect of the present invention to provide a method for employing an RMA applicator and means to display images of a subject for cosmetic enhancement.

It is another aspect of the present invention to provide a method to let users select and display cosmetic enhancements of digital images of subjects.

It is still another aspect of the present invention to provide a method to let users automatically apply RMA to subjects to achieve cosmetic enhancement based on selections made to images on computer displays.

These and other aspects, features, and advantages are achieved according to the system and method of the present invention. In accordance with the present invention, an automated cosmetic applicator uses at least one wide-angle camera and at least one high resolution camera to capture images of a surface such as the human body. A process of differential lighting is used during capture of the images with the high-resolution camera to identify texture. The resulting images contain rich, pixel-level data about the subject's color, light value and texture characteristics. Software analyzes images to identify large and small features of the surface and to use these features as landmarks to create a corresponding map in computer memory. Software then uses this map to calculate cosmetic enhancements to aspects of the surface and to determine the position the applicator for accurate deposition of the cosmetics to achieve the enhancements. One or more accelerometers are added to the applicator to provide data that increases the accuracy of the map and of the positioning of the applicator. Software uses the map to provide "pix-rich" files, high-resolution realistic image files about the subject that are also data rich. Pix-rich files can be displayed and further modified for use as simulated still and video 3D images, for example in video games and animations.

In accordance with the present invention, an applicator head on a reflectance modifying agent (RMA) applicator scans an area on a user, such as a face. It uses software to sense aspects of color and texture, map the area, and automatically calculate cosmetic enhancements. One or more digital images representing the scan, mapping, and cosmetic enhancements are stored in computer memory. A user employs computer controls to view one or more images of the original scan and possible cosmetic enhancements on a computer display and to select and modify desired virtual cosmetic enhancements. Subsequently the user employs the applicator head on the RMA applicator to automatically apply RMA to the actual area to achieve the specified enhancements. During this process, landmarks on the area are used for registration to create the map of the area, to track virtual enhancements and to enable accurate positioning of the applicator head subsequently for precise application of the RMA to the area.

BRIEF DESCRIPTION OF THE DRAWINGS

The following embodiment of the present invention is described by way of example only, with reference to the accompanying drawings, in which.

DETAILED DESCRIPTION OF EMBODIMENT

Determining Head Position by Tracking Large and Small Features

The referenced U.S. patent application Ser. No. 11/503,806 describes a computer-controlled system and method for scanning an area of human skin or other feature and automatically identifying unattractive attributes in that area, calculating cosmetic enhancements, and automatically applying RMA, typically through inkjet printing, to make those enhancements to that area.

The U.S. patent application Ser. No. 12/028,835 "HAND-HELD APPARATUS AND METHOD FOR THE AUTOMATED APPLICATION OF COSMETICS AND OTHER SUBSTANCES" describes an applicator head with raised contact means, such as pounce wheels, for moving an RMS applicator over a surface.

One aspect of the present invention is the creation of rich image files that can be displayed and further modified for use as simulated still and video 3D images, for example in video games and animations. In this patent application, Pix-Rich™ files are files that contain rich, pixel-level data about a subject's color, light value and texture characteristics.

The present invention comprises innovations to the system and method that provide efficient tracking of the position of large features on the human body and smaller features on areas of skin and of the position of a cosmetic applicator relative to those features.

Apparatus for Scanning and Applying Cosmetics

The following section explains one embodiment of an apparatus that scans a surface, calculates cosmetic enhancements, and applies reflectance modifying agents (RMAs) and that may also be used to provide data for pix-rich files.

Figure 1:
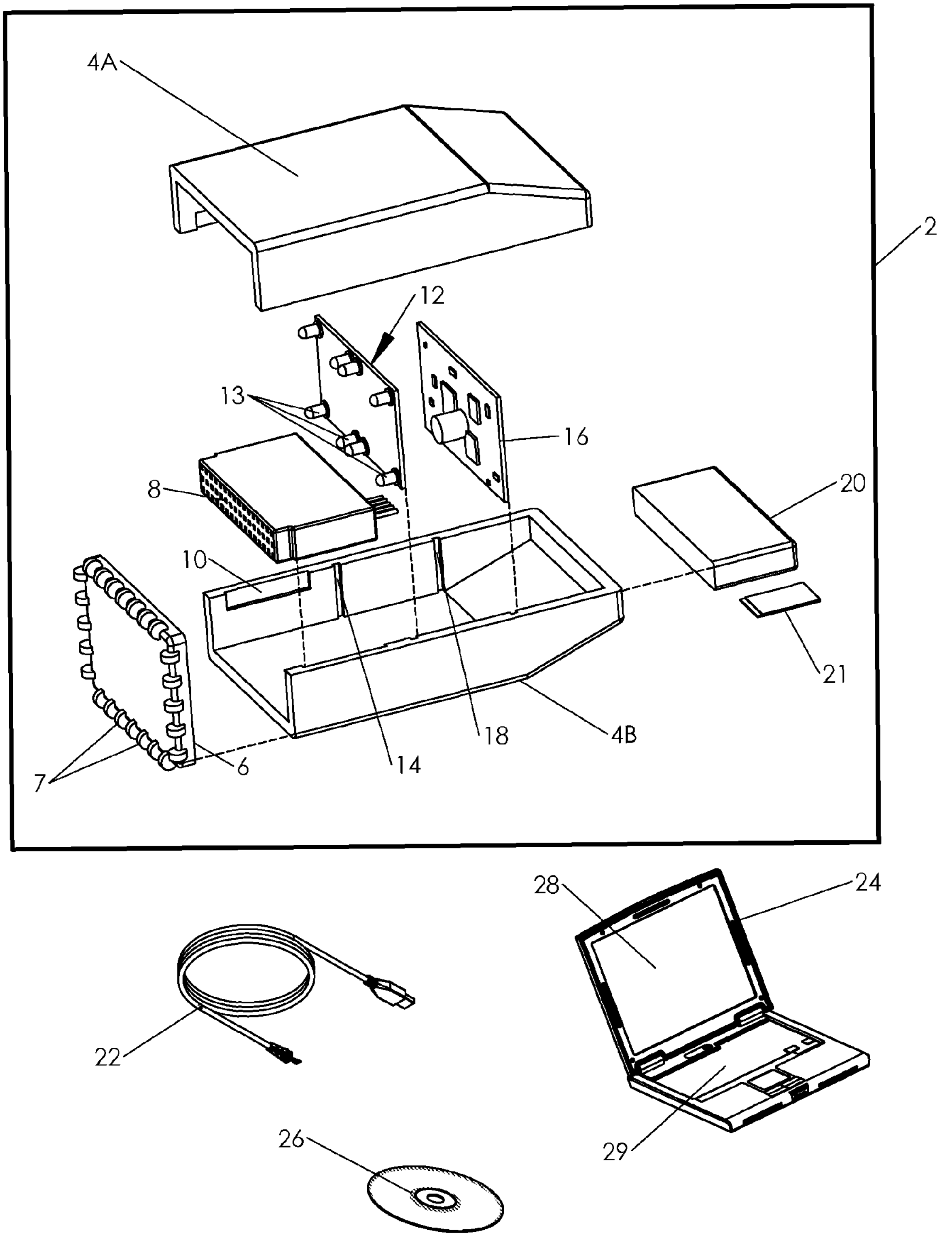
FIG. 1 is a block diagram that illustrates elements of an RMA applicator head and a computer with a display and controls.

The applicator head 2, shown in FIG. 1, covers an area of skin about equal to a single electric razor head. Such a size is proven daily to fit in intimate contact across a human face. In an embodiment for speed of application, multiple applicator heads 2 may be assembled in a floating mount, just as multiple floating heads are combined in a single electric razor.

Elements

The applicator head 2 comprises the following elements.

Plastic Case

The molded case 4A and 4B has rubber "O" type rings for waterproofing, so that the applicator head 2 can be run under the faucet for cleaning, like a razor. The inkjet printer head 8 can be maintained this way, which is not an option in normal printers. In an embodiment, the applicator head 2 may "park" for storage on a stand that would cap the applicator head 2.

Floating Ring

In one example, the applicator head 2 is moved across the skin by means of a floating ring 6 with pounce wheels 7, which are wheels with points around their outer rims.

The height of the points maintains a proper distance from the surface for both scanning and inkjet deposition. The pounce wheels 7 also reduce the amount of outside light entering around the base of the applicator to prevent distorting the accuracy of the scanning. In addition, the points on the pounce wheels 7 limit contact of the applicator head 2 with the cosmetics being deposited, to prevent smudging. Thus, they will typically leave behind minimal deposits of the RMA as they are moved over surfaces.

The pounce wheels 7 should be made of durable non-absorptive and hydrophobic material, for example silicon rubber or Teflon, so that they last and do not absorb the RMA. Their heights should also be low, for example 3/16 of an inch (4.8 mm). The use of low heights keeps the system close to the surface so that too much light does not come in underneath the system. The pounce wheels 7 may further be colored black to help absorb light. Their widths should be narrow to further reduce the area that comes into contact with the RMA. Their points should not be very sharp, so that they will not easily puncture surfaces such as skin.

In an embodiment, the pounce wheels 7 may be mounted on thin wires serving as axles.

In an embodiment, twelve pounce wheels may be mounted on each side of the floating ring 6.

In an embodiment, a non-contact, electrostatic wipe (not shown) may be used to blow off the RMA from the pounce wheels 7.

Inkjet Head

A very thin inkjet head 8 fits perpendicularly to the skin into case groove 10.

Field Lens

A field lens 12 with LED assembly 13 provides telecentric viewing so that size is independent of distance and the view fits around the inkjet head. It fits into case groove 14 and helps protect the electronics behind the lens from water and dirt.

Camera

A high-resolution camera module 16 with electronics fits into case groove 18. In an embodiment, the high-resolution camera module 16 may be a module made for mobile devices such as cell phones. The newer of these modules have 3 megapixels and above. In covering an area half an inch across, just a 1 megapixel camera would have four times the resolution of the human eye at 10 inches (25 cm).

Cosmetic Reservoir

A replaceable cosmetics reservoir 20 and ink is shown only as a block, but it should have a visually appealing and protectable design because it is what consumers would actually buy repeatedly, like razor blades. In an embodiment, the cosmetics reservoir 20 may contain multiple separate RMA colors that may be mixed to achieve desired effects. In another embodiment, it may contain a single RMA color premixed to achieve a desired aim color or effect.

Attachments

In an embodiment, the applicator head 2 is attached to the elements given below.

Cable

In one embodiment, a data and power cable 22 is required. A USB 2.0 cable may be used.

Computer

A consumer computer 24 is required. Almost any newer computer configured correctly with enough disk memory, good display, and a USB port may be used.

The computer 24 further comprises a display 28 and controls 29, both known to those skilled in the art.

Software

Software 26 is required that runs on the computer 24 and provides the functionality for scanning an area of a human feature, such as skin, calculating cosmetic enhancements, tracking registration, and applying the RMA, explained in detail in the cross-referenced application and outlined below.

In an embodiment, the software 26 also enables users to employ the RMA applicator head 2, the display 28, and the controls 29 to view stored digital images of the scanned surface so that they can make virtual cosmetic enhancements to those images and so that they can automatically and precisely apply RMA to that surface to achieve those enhancements.

Wide-Angle Cameras

Figure 2A:
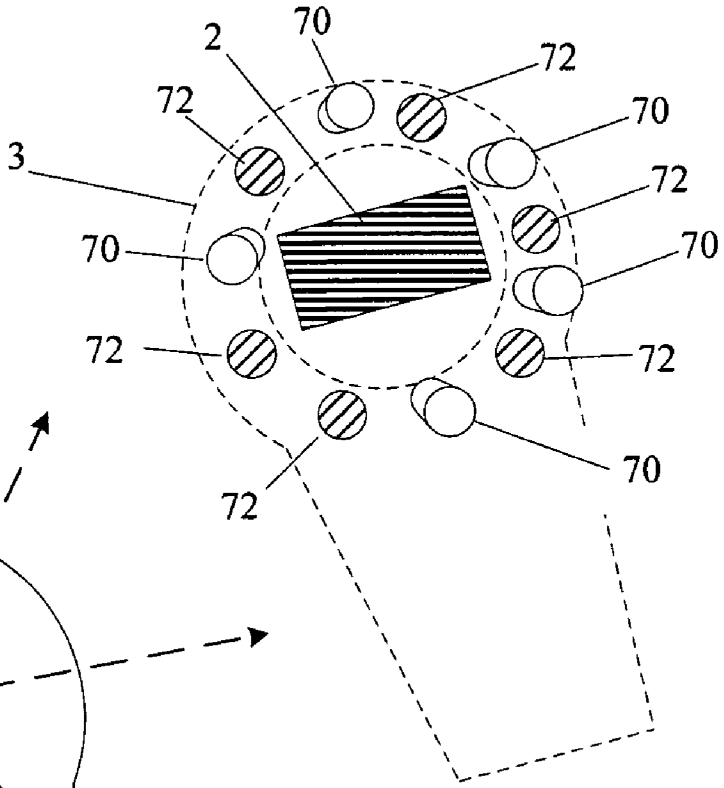
FIG. 2A is a representative diagram that illustrates wide-angle cameras and accelerometers mounted on an RMA applicator.

One or more wide-angle cameras 70, shown in an embodiment in FIG. 2A, may be attached to the applicator 3.

Figure 2B:
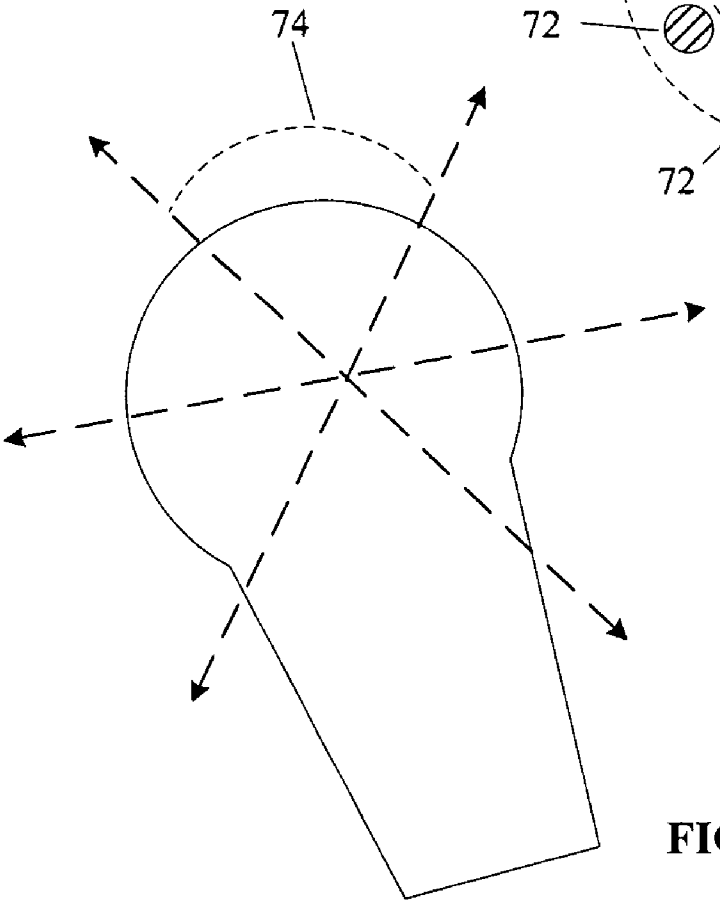
FIG. 2B is a representative diagram that illustrates a top view of an RMA applicator showing the field of view of its wide-angle cameras.

In an embodiment, six miniature wide-angle cameras 70 may be used, each wide-angle camera 70 covering a field of view 74, shown in FIG. 2B, that is approximately 60° or more of the visual area below and around the applicator head 2, so that 360° of the surface to be scanned is covered.

In this embodiment, the wide-angle cameras 70 are mounted on the side of the applicator 3, around one or more applicator heads 2, shown in FIG. 1, and look out and down, similar in topology to the eight eyes of a wolf spider, which provide vision around the spider. Wide-angle cameras 70, shown in FIG. 2A, may thus be considered analogous to the visual element and are used for identifying the location of large features, such as bone structures, lips, and eyes, on the surface of the body and the position of the applicator 3 relative to that surface. Such slow movements may be characterized as providing low frequency data.

Some overlap in the images captures by the wide-angle cameras 70 may be useful for identifying the location of large features and the position of the applicator 3 relative to the surface.

In an embodiment, a camera may be focused on a mirror to expand the visual area of the camera. For example, a 360° mirror may enable a camera to operate as a wide-angle camera, as is known to those skilled in the art.

Accelerometers

One or more accelerometers 72 may be used to measure the acceleration to give very precise tracking of rapid movements of the applicator 3. Such rapid movements may be characterized as providing high frequency data. The use of accelerometers 72 enables tracking of the frame-by-frame location of the applicator 3, relative to aspects of the surface being scanned.

For example, piezo accelerometers, known to those skilled in the art, may be used. In an embodiment, six piezo accelerometers 72 may be used around the sides of the applicator 3, to provide data about movement along the X, Y, and Z axis of the applicator, representing pitch, yaw, and roll.

Accelerometers 72 may thus be considered analogous to an inner positioning sense, such as that of the human inner ear.

Method of Operation

The present invention requires a complex software method to manage precision mapping of the whole body surface, similar to the problems that have been solved in gaming and modern animation. The general steps of this method are illustrated in FIG. 3.

Figure 3:
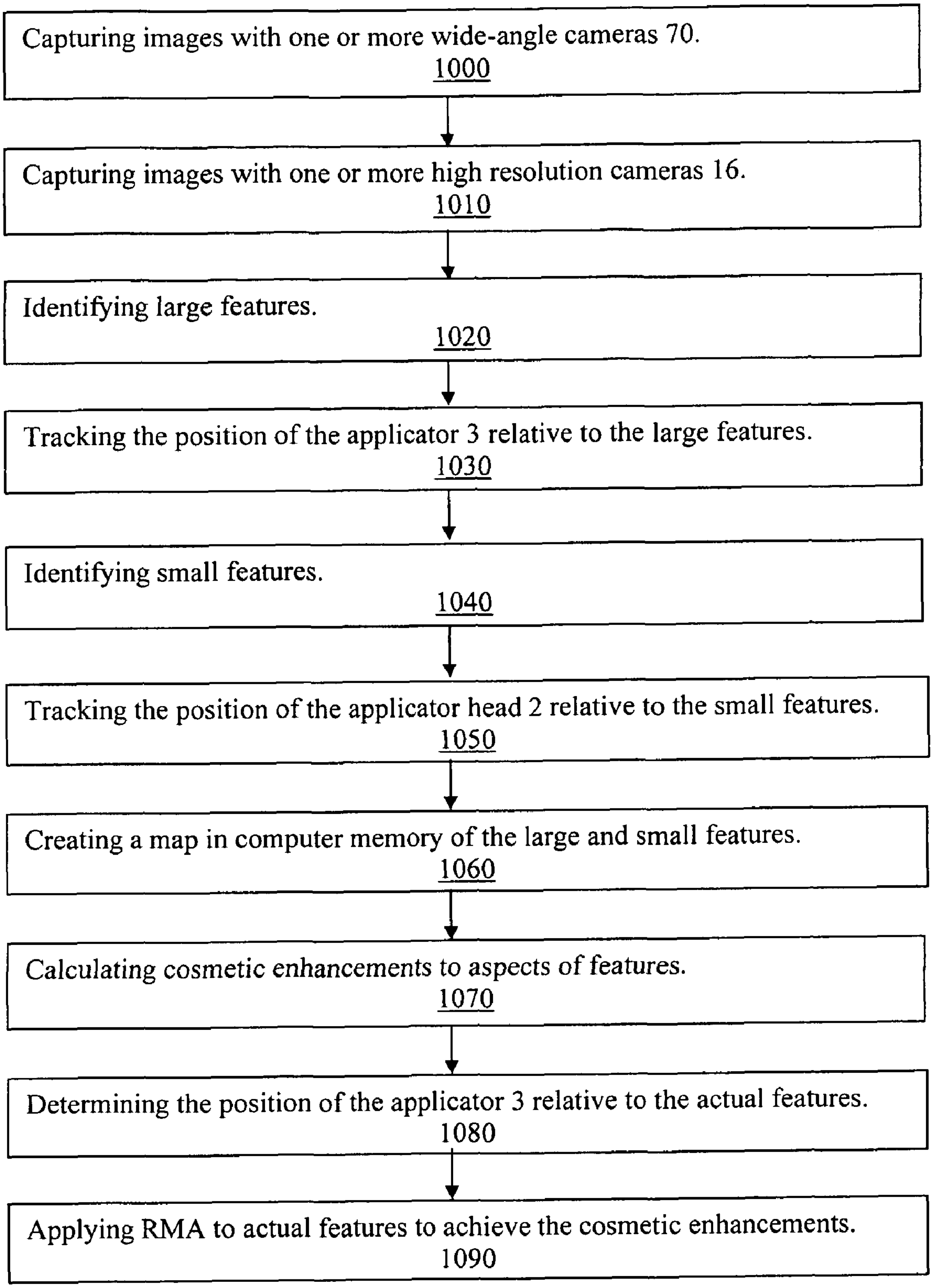
FIG. 3 is a flow chart illustrating the general steps for determining the location of features on a surface such as the human body for mapping and the deposition of cosmetics.

Step 1000 in FIG. 3—Capturing Images with One or More Wide-Angle Cameras In an embodiment, the user moves the applicator 3, shown in FIG. 2A, inward toward the body to make contact with the skin, and the computer 24, shown in FIG. 1, receives exposures representing an expanding view of the area of the surface of the body from the wide-angle cameras 70, shown in FIG. 2A. These exposures feed the computer 24, shown in FIG. 1, landscape data showing the direction and proximity to large nearby features such as eyes, lips, breasts, and bone structures such as knees, and monitors the disposition and motion of limbs. After the applicator head 2, shown in FIG. 1 makes contact with the skin, the wide-angle cameras 70, shown in FIG. 2A, continue to feed the computer this landscape data about large features.

The wide-angle cameras 70 thus act analogously to the sensors on a Lunar Lander, which map large landmarks on the surface of the moon.

Step 1010 in FIG. 3—Capturing Images with One or More High Resolution Cameras In an embodiment, after the applicator head 2, shown in FIG. 1, makes contact with the skin, the user moves the applicator head 2, anywhere over the skin, much like using an electric razor. For example, the user may move the applicator head 2 over an area of skin 302, shown in FIG. 4, in path of movement 30.

Figure 4:
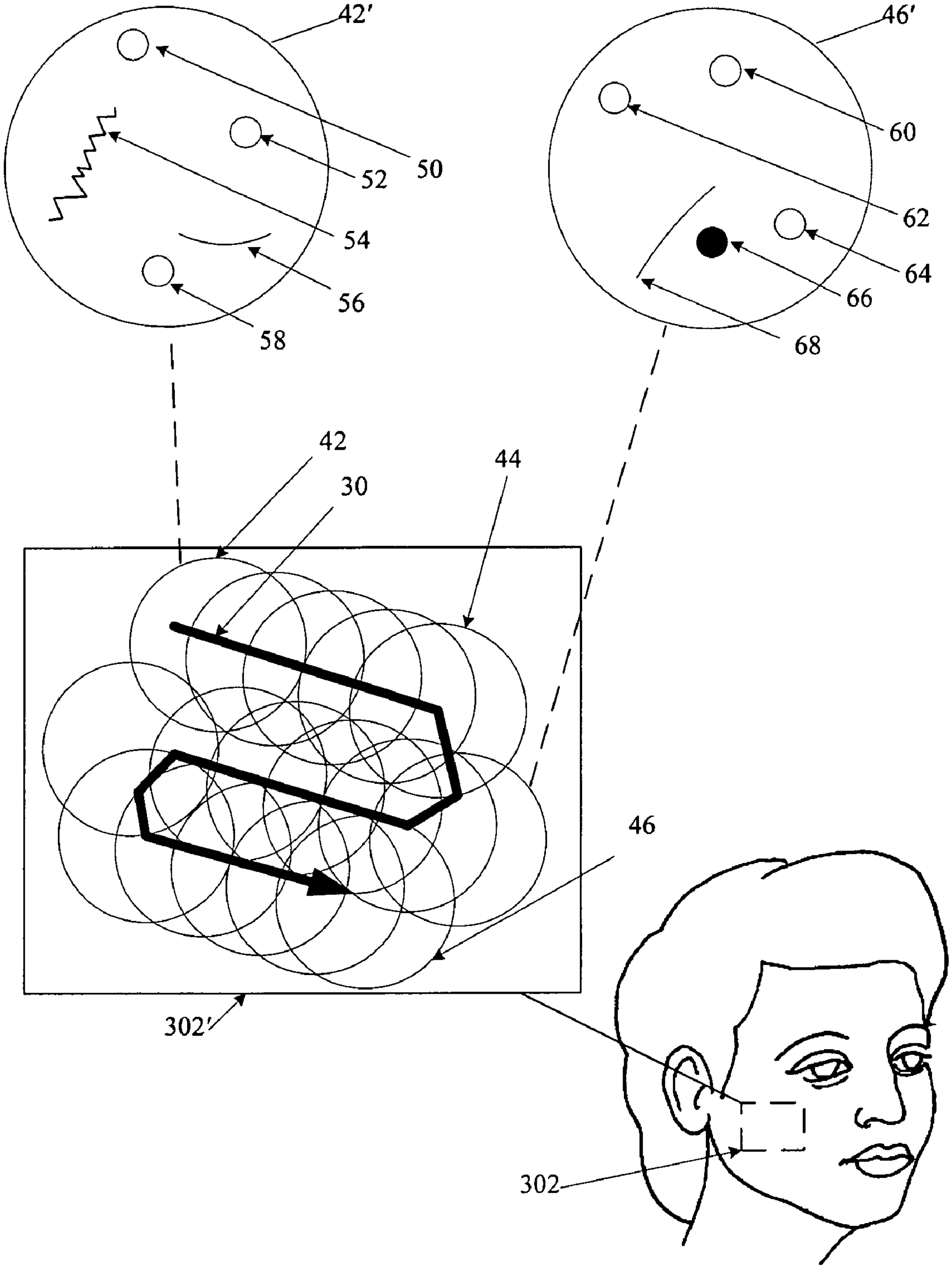
FIG. 4 is a representative diagram illustrating a path of movement of the applicator head over an area of skin whereby multiple overlapping images may be captured.

The camera module 16, shown in FIG. 1, then captures overlapping images, preferably at least 10 per second, from the area of skin 302, shown in FIG. 4, under applicator head 2, shown in FIG. 1. Most of the image at each capture is redundant with the previous capture. For example, images 42, 44, and 46, shown in FIG. 4, are captured.

In an embodiment, an audible signal from a sound source, for example buzzer 21, shown in FIG. 1, guides the user to completion of each area, In another embodiment, the motion and action of the applicator head 2 is tracked on the computer display 28.

In another embodiment, the user always starts an applicator session at a fixed point, such as the top center of the forehead, waits for a buzz sound to confirm acquisition of data, and scans from the touchdown point in a defined pattern, for example back and forth left and right moving the applicator head 2 down about ⅛ width on each pass. In this way, software 26 has the simplified task of staying locked on position rather than tracking complex and arbitrary non-overlapping movements.

Step 1020 in FIG. 3—Identifying Large Features

In an embodiment, the software 26, shown in FIG. 1, analyzes the exposures from the wide-angle cameras 70, shown in FIG. 2A, in comparison with at least one generic map of large human features previously stored in computer memory, for example in the non-volatile memory of computer 24, shown in FIG. 1.

Such generic maps of human features are used in the gaming and animation industries, known to those skilled in the art. An example is Optasia™, the model-based feature-recognition platform developed by Image Metrics, Plc. The "Technical White Paper" on the Image Metrics website states that, "The Optasia engine can perform rapid model-to-image matching regardless of the model type, including those with high-frequency elements such as texture."

Thus, software 26 can identify the location of large features from the data received from the wide-angle cameras 70, shown in FIG. 2A.

Step 1030 in FIG. 3—Tracking the Position of the Applicator Relative to the Large Features Software 26, shown in FIG. 1, also calculates the position of the applicator 3, shown in FIG. 2A, in relation to the location of the large features that it has identified.

A visual position sense, resulting from the wide-angle cameras 70, shown in FIG. 2A, is accurate at low frequencies. In fact, because averaging can be used, it is more accurate at low frequencies. The wide-angle cameras 70 can find position and monitor very slow movements accurately.

Using Accelerometers

In an embodiment comprising one or more accelerometers 72, shown in FIG. 2A, the software 26, shown in FIG. 1, further calculates the position of the large features and of the applicator 3, shown in FIG. 2A, based on rapid movements of the applicator 3.

In this tracking process, all the sensors thus continuously refine calibration during each applicator session as the precision motion measured by visual trains the gain and offset of the sensors. This is the relationship between the human visual and positional sensors.

An accelerometer 72, shown in FIG. 2A, is useless at finding absolute position (DC), but it can accurately track fast movements, up to audio frequencies at which visual is useless, and in fact can be used as a microphone. In between, there is a crossover frequency for which the two measurements, from the wide-angle cameras 70 and from the accelerometers 72, can be crossed over, like a woofer and tweeter. Around this frequency range the visual position is used to adjust and continuously refine the gain and offset of the accelerometer 72. In the applicator 3, this crossover may be at around 1 Hz, in an embodiment.

Step 1040 in FIG. 3—Identifying Small Features

Software 26, shown in FIG. 1, analyzes the captured images from the high-resolution camera 16, such as images 42, 44, and 46, shown in FIG. 4, and identifies landmarks, or "skinmarks" in those images. Many aspects of human features may be used as skinmarks, for example, pores, moles, scars, lines, wrinkles, age spots, sun damage, freckles, color variations, contours of features, and textural variations such as bumps. For example, an expanded view 42' of captured image 42 represents a distinctive pattern of skinmarks: a pore 50, another pore 52 in a different location, a scar 54, a wrinkle 56, and a third pore 58 in yet another location. Expanded view 46' of captured image 46 represents a different distinctive pattern: a pore 60, another pore 62, a third pore 64, a mole 66, and a wrinkle 68.

In general, each type of skinmark has distinctive characteristics that can be identified from the scanned data, based on empirical studies of scanned skinmarks. Examples of such characteristics are explained in the cross-referenced patent application.

In an embodiment, an applicator 3, shown in FIG. 2A, may comprise multiple applicator heads 2, shown in FIG. 1, and so employ multiple high-resolution cameras 16 to capture images that can be analyzed to identify skinmarks.

Step 1050 in FIG. 3—Tracking the Position of the Applicator Head Relative to the Small Features The positional information provided by the skinmarks described above enables the software 26, shown in FIG. 1, to keep the applicator head 2, the area of skin 302, shown in FIG. 4, and computer models in register. Thus, whenever the applicator head 2, shown in FIG. 1, is placed on the skin, software 26 can track where applicator head 2 is located relative to the skinmarks on a global map, described below, while the global map is being assembled, using the skinmarks as they are identified, and after the whole map, containing all the skinmarks, has been completed.

In a worst case scenario, the software 26 may have to process a large area of the skin to find a non-redundant set of skinmarks for tracking.

Using Accelerometers

In an embodiment comprising one or more accelerometers 72, shown in FIG. 2A, the software 26, shown in FIG. 1, further calculates the position of the small features and of the applicator head 2 based on rapid movements of the applicator 3, shown in FIG. 2A.

As mentioned above, in this tracking process all the sensors thus continuously refine calibration during each applicator session as the precision motion measured by visual trains the gain and offset of the sensors. This is the relationship between the human visual and positional sensors.

Figure 5:
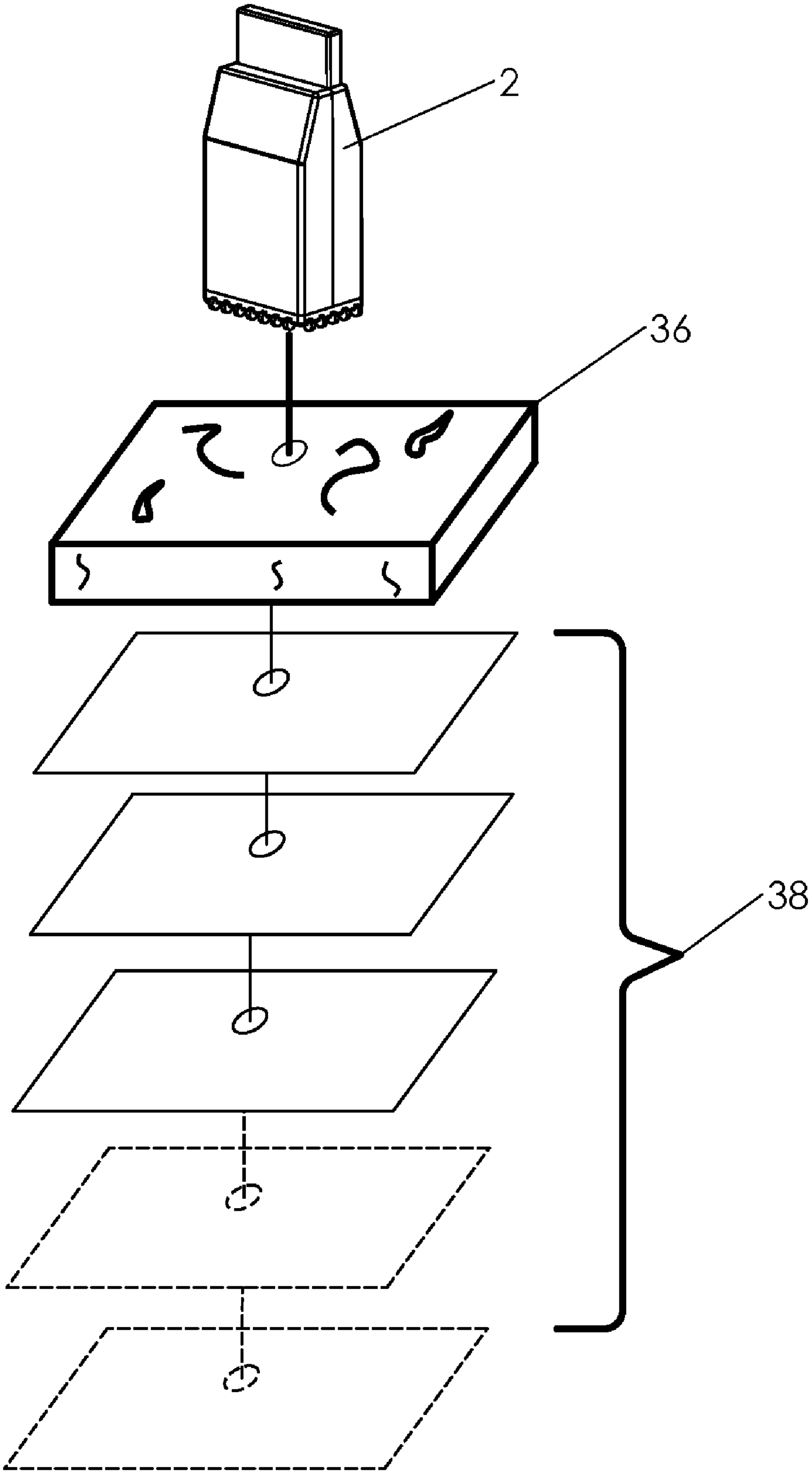
FIG. 5 is a representative diagram illustrating aspects associated with the present invention that require registration.

Step 1060 in FIG. 3—Creating a Map in Computer Memory of the Large and Small Features As shown in FIG. 5, the method of the present invention requires knowledge of applicator head 2 position relative to real skin 36 and other features and a mapping from real skin 36 and other features to abstract layers 38 in computer memory that model that skin and other features, describe aesthetic choices, guide execution strategies, and track long-term changes in the appearance of the skin and other features.

Software 26, shown in FIG. 1, uses the large and small features it has identified relative to the position of the applicator 3, shown in FIG. 2A, to assemble a global map of the scanned surface and store it in computer memory, for example on computer 24, shown in FIG. 1. Moreover, the global map can be continually revised each time the applicator 3, shown in FIG. 2A, is moved to scan an additional area of skin or other feature, so that a global map of the entire desired area of the skin can be assembled and revised through further scanning.

In an embodiment, the global map is stored automatically at periodic intervals. In another embodiment, it is stored each time the applicator head 2, shown in FIG. 1, is raised from the surface being scanned. Thus, the global map enables registration of applicator position, scanned surface, and computer strategy layers through time between applications sessions and even days.

If given the picture of a city, including many streets, houses, and trees, one could track where in the city the area was, even if some of the houses changed and the leaves changed color for autumn. In a similar way, changes in human features such as living skin, for example color changes and the appearance of new wrinkles, do not impede the accuracy of overall tracking through the global map.

In an embodiment, the computer map tracks the skeletal structure of a human body, bone by bone and joint by joint, from images captured by the wide-angle cameras 70, shown in FIG. 2A. Small features on the surface of the skin are referenced by their position relative to underlying bone structure, in whatever way that bone structure moves, so that a frexel, or area of skin, keeps a constant position relative to this complex system even during active motion of the body.

Frexels

In this patent specification, the term "frexel" is defined as a small pixel-like region of the skin. A frexel might correspond to a small portion of a freckle or other skin feature, or it may correspond to an area of the skin that does not have special features. A frexel thus refers to skin rather than to an independent coordinate system. The term frexel is used to suggest that what is being measured is on a 3-D surface rather than a flat surface.

Step 1070 in FIG. 3—Calculating Cosmetic Enhancements to Aspects of Features Automatic Enhancements In an embodiment, the software 26, shown in FIG. 1, can automatically calculate and, in an embodiment display, cosmetic enhancements to the features using the methods described in the cross-referenced patent application. For example, these enhancements can be for smoothing skin, lightening skin, camouflaging blemishes, and making freckles crisper.

In addition, the software 26 can carry out overall enhancements based on input by designers' looks, like an evening look or a Nicole Kidman look. One embodiment of this technique is described in the referenced provisional patent applications.

These automatic enhancements may be done automatically or in response to user selections.

User Input

In an embodiment, the user can specify all or part of the enhancements, including modifications of automatic enhancements.

Step 1080 in FIG. 3—Determining the Position of the Applicator Relative to the Actual Features After the enhancements have been calculated, the user again moves the applicator 3, shown in FIG. 2A, over the surface to be cosmetically enhanced. The wide-angle cameras 70, shown in FIG. 2A, and the high-resolution camera 16, shown in FIG. 1, again capture images of the surface.

Software 26 again identifies large and small features of the scanned surface and the position of the applicator 3, shown in FIG. 2A, relative to landmarks and skinmarks in the global map of the scanned surface. Thus, software 26 can determine the position of the applicator relative to actual features.

In an embodiment comprising one or more accelerometers 72, shown in FIG. 2A, the software 26, shown in FIG. 1, further calculates the position of the large and small features and of the applicator 3, shown in FIG. 2A, based on rapid movements of the applicator 3.

Step 1090 in FIG. 3—Applying RMA to Actual Features to Achieve the Cosmetic Enhancements When the software 26, shown in FIG. 1, determines that an area of skin or other feature for which an enhancement has been specified is underneath the inkjet head 8, it instructs the inkjet head 8 to apply the RMA, contained in the cosmetic reservoir 20, to accomplish the enhancement.

In an embodiment, the RMA can be deposited on multiple passes of the applicator head 2 over the skin until the chosen enhancement is accomplished. Then no more RMA is deposited on subsequent passes.

The entire process of scanning, making virtual enhancements, and applying RMA may be repeated to the user's satisfaction.

Creating Pix-Rich Files

In an innovation to the system and method described above, the detailed, highly accurate global maps created for cosmetic enhancements are saved as pix-rich files. These pix-rich files may then be moved to any computer device and used as digital images for any virtual display, for example in gaming, animation, cell phone, and medical applications. For example, the planes of data in the global maps may be saved, partially or as a whole, as compressed JPEGF files, known to those skilled in the art.

Richer, More Manipulable Data for Realistic Simulations

Pix-rich files are a new medium because the data they provide about a scanned surface is much richer in positional information, reflectance (RGB) and topographical (texture) data than the data in previous files of scanned images or photographs. For example, the technique of differential lighting, explained in the cross-referenced patent applications, provides greatly increased data about the topology of a scanned surface, showing more information about large and small features, from eyes and cheekbones down to the level of pores in the skin. In addition, more data is obtained because many different frames of scanned data about small pieces of the surface and are the put together to assemble the global maps. This further provides very high resolution data about the surface.

As a result, pix-rich files can provide much more realistic images of people for simulated images, greatly reducing the problem of over-smoothness.

Because they provide richer data, they are also dynamically manipulable electronically. That is, they are much easier to manipulate by software, such as gaming or animation applications, because such software does not have guess and calculate for as much missing information or work as hard to recognize feature to create simulate images.

Availability

Pix-rich images will be potentially much more available to uses through home scanning embodiments of the cosmetic scanning and application system described above.

User Enhancements

Users will be able to use home scanning embodiments of the cosmetic scanning and application system described above to cosmetically enhance images of themselves that can be saved as pix-rich files. This will help users be able to present simulated images of themselves as they want to be seen.

Alternate Embodiments

Other Hardware Configurations

The applicator head 2, shown in FIG. 1, is attached to a separate computer 26 with a display 28 and controls 29. In another embodiment, the applicator head 2 may comprise an element of an RMA applicator that itself is a computerized device with non-volatile memory, a display, and controls, so that no separate computer is required as an attachment.

Application of Other Substances than RMAs

The applicator head 2 of the present invention may be used to apply other substances than RMAs, for example medically beneficial compounds or live skin.

Application to Other Area than Skin

The applicator head 2 of the present invention may be used to apply RMAs and other substances to other areas than human skin. For example, it may apply substances to fabrics, fruit, walls, leaves, and flowers.

Other Uses for Global Maps

The detailed, highly accurate global maps created for cosmetic enhancements may be used as digital images for any virtual display, for example in gaming, animation, cell phone, and medical applications.

Whole Body Cosmetic Enhancement

Method of Operation

A typical use of the present invention is for making cosmetic enhancements to a person's face, but analogous enhancements could be made to any other area of the human body or other surfaces. In the explanation of the present invention's method given below, the face is use as a specific example and further represents any area of human skin, any human feature, or any other surface to be enhanced. The general steps of this method are illustrated in FIG. 6.

Figure 6:
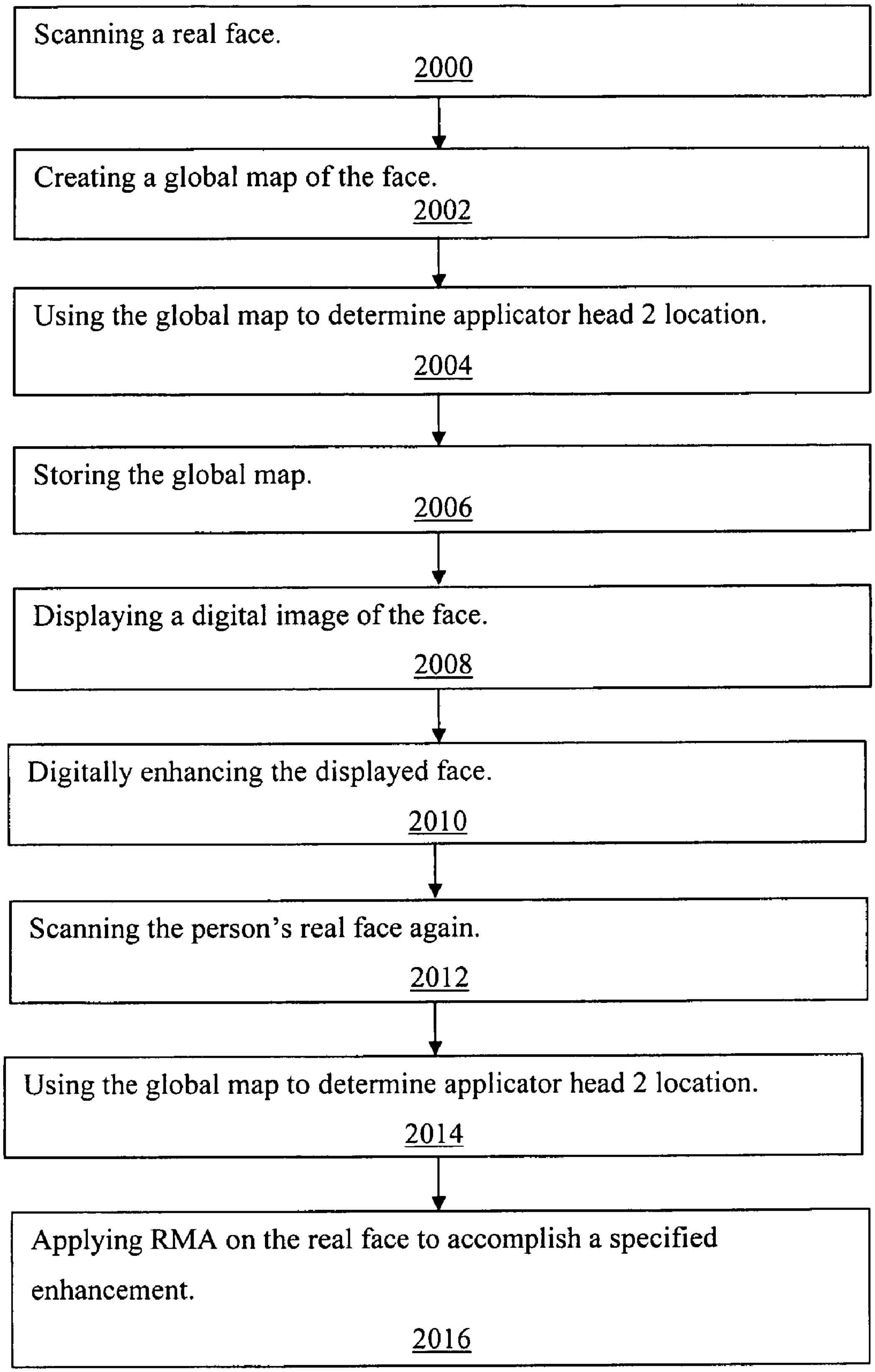
FIG. 6 is a flow chart illustrating the general steps for using the applicator head, computer display, and computer controls to select virtual cosmetic enhancements and apply RMA to achieve them on actual area.

Step 2000 in FIG. 6—Scanning a Real Face.

In an embodiment, the user moves the applicator head 2, shown in FIG. 1, anywhere over the face, very much like using an electric razor. For example, the user may move the applicator head 2 over an area of skin 302, shown in FIG. 4, in path of movement 30. The face may be that of the user or any one else.

The camera module 16, shown in FIG. 1, then captures overlapping images, at least 10 per second, from the area of skin 302, shown in FIG. 4, under applicator head 2, shown in FIG. 1. Most of the image at each capture is redundant with the previous capture. For example, images 42, 44, and 46, shown in FIG. 4, are captured.

In an embodiment, an audible signal from a sound source, for example buzzer 21, shown in FIG. 1, guides the user to completion of each area, In another embodiment, the motion and action of the applicator head 2 is tracked on the computer display 28.

In another embodiment, the user always starts an applicator session at a fixed point, such as the top center of the forehead, waits for a buzz sound to confirm acquisition of data, and scans from the touchdown point in a defined pattern, for example back and forth left and right moving the applicator head 2 down about ⅛ width on each pass. In this way, software 26 has the simplified task of staying locked on position rather than tracking complex and arbitrary non-overlapping movements.

Step 2002 in FIG. 6—Creating a Global Map of the Face.

As shown in FIG. 5, the method of the present invention requires knowledge of applicator head 2 position relative to real skin 36, and a mapping from real skin 36 to abstract layers 38 in computer memory that model that skin, describe aesthetic choices, guide execution strategies, and track long-term changes in the appearance of the skin.

To track positioning, the software 26 analyzes the captured images of the face, such as images 42, 44, and 46, shown in FIG. 4, and identifies landmarks, or "skinmarks" in those images. Many aspects of human features may be used as skinmarks, for example, pores, moles, scars, lines, wrinkles, age spots, sun damage, freckles, color variations, contours of features, and textural variations such as bumps. For example, an expanded view 42' of captured image 42 represents a distinctive pattern of skinmarks: a pore 50, another pore 52 in a different location, a scar 54, a wrinkle 56, and a third pore 58 in yet another location. Expanded view 46' of captured image 46 represents a different distinctive pattern: a pore 60, another pore 62, a third pore 64, a mole 66, and a wrinkle 68.

Software 26, shown in FIG. 1, identifies such distinctive patterns of skinmarks in each captured image, such as 42, 44, and 46, shown in FIG. 4, in an area of skin 302 and uses them to assemble a global map of the face. Moreover, the global map can be continually revised each time the applicator head 2 is moved to scan an additional area of skin or other feature, so that a global map of the entire desired area of the face can be assembled and revised through further scanning.

Step 2004 in FIG. 6—Using the Global Map to Determine Applicator Head 2 Location.

The positional information provided by the skinmarks described above enables the software 26, shown in FIG. 1, to keep the applicator head 2, the area of skin 302, shown in FIG. 4, and computer models in register. Thus, whenever the applicator head 2 is placed on the face, software 26, shown in FIG. 1, can track where applicator head 2 is located relative to the skinmarks on the global map, while the global map is being assembled, using the skinmarks as they are identified, and after the whole map, containing all the skinmarks, has been completed.

In a worst case scenario, the software 26 may have to process a large area of the face to find a non-redundant set of skinmarks for tracking.

Step 2006 in FIG. 6—Storing the Global Map.

An innovation is that software 26, shown in FIG. 1, stores the global map in non-volatile memory on the computer 24. In an embodiment, the global map is stored automatically at periodic intervals. In another embodiment, it is stored each time the applicator head 2 is raised from the face.

Thus, the global map enables registration of applicator head 2 position, skin, and computer strategy layers through time between applications sessions and even days.

If given the picture of a city, including many streets, houses, and trees, one could track where in the city the area was, even if some of the houses changed and the leaves changed color for autumn. In a similar way, changes in living skin, such as color changes and the appearance of new wrinkles, do not impede the accuracy of overall tracking through the global map.

Step 2008 in FIG. 6—Displaying a Digital Image of the Face.

After the global map has been stored, a user can use the computer controls 29, shown in FIG. 1, to display a high level, representative image of the face on the computer display 28. The displayed image is a richly detailed digital image.

Step 2010 in FIG. 6—Digitally Enhancing the Displayed Face.

The user can then employ the computer controls 29, shown in FIG. 1, to make virtual cosmetic enhancements to the displayed image of the face, for example to change areas of coloring or to achieve an overall "look." Software 26 correlates the virtual enhancements with the appropriate skinmarks in the global map.

In different embodiments, the virtual enhancements can be made automatically and through specific user input.

Automatic Enhancements

In an embodiment, the software 26 can automatically calculate and display virtual cosmetic enhancements to the area of skin 302 using the methods described in the cross-referenced patent application. For example, these enhancements can be for smoothing skin, lightening skin, camouflaging blemishes, and making freckles crisper.

In addition, the software 26 can carry out overall enhancements based on input be designers looks, like an evening look or a Nicole Kidman looks. One embodiment of this technique is described in the referenced provisional application.

These automatic enhancements may be done automatically or in response to user selections.

User Input

In an embodiment, the user can specify all or part of the virtual enhancements, including modifications of automatic enhancements.

Step 2012 in FIG. 6—Scanning the Person's Real Face Again.

After the user has selected one or more desired virtual enhancements, the user again moves the applicator head 2, shown in FIG. 1, over the face. The applicator head 2 again captures images of the face.

Step 2014 in FIG. 6—Using the Global Map to Determine Applicator Head 2 Location.

Software 26, shown in FIG. 1, analyzes the skinmarks in the captured images and correlates those skinmarks with the ones stored in the global map to determine the position of the applicator head 2 relative to locations on the face for which virtual enhancements have been specified.

Step 2016 in FIG. 6—Applying RMA on the Real Face to Accomplish a Specified Enhancement.

When the software 26, shown in FIG. 1, determines that an area of the face for which a virtual enhancement has been specified is underneath the inkjet head 8, it instructs the inkjet head 8 to apply the RMA, contained in the cosmetic reservoir 20, to accomplish the enhancement.

In an embodiment, the RMA can be deposited on multiple passes of the applicator head 2 over the face until the chosen enhancement is accomplished. Then no more RMA is deposited on subsequent passes.

The entire process of scanning, making virtual enhancements, and applying RMA may be repeated to the user's satisfaction.

Other Hardware Configurations

The applicator head 2, shown in FIG. 1, is attached to a separate computer 26 with a display 28 and controls 29. In another embodiment, the applicator head 2 may comprise an element of an RMA applicator that itself is a computerized device with non-volatile memory, a display, and controls, so that no separate computer is required as an attachment.

Application of Other Substances than RMAs

The applicator head 2 of the present invention may be used to apply other substances than RMAs, for example medically beneficial compounds or live skin.

Application to Other Area than Skin

The applicator head 2 of the present invention may be used to apply RMAs and other substances to other areas than human skin. For example, it may apply substances to fabrics, fruit, walls, leaves, and flowers.

It will be apparent to those skilled in the art that different embodiments of the present invention may employ a wide range of possible hardware and of software techniques. The scope of the current invention is not limited by the specific examples described above.

What is claimed is:

1. An applicator for an apparatus to improve the visual attractiveness of a region human skin by applying a reflectance modifying agent, the applicator comprising a reflectance modifying agent applicator head, comprising
- a case,
- an inkjet printer head;
- a telemetric field lens;
- a plurality of wide-angle cameras comprising at least two miniature wide-angle cameras, outwardly and downwardly aimed relative to the case, such that each wide-angle camera has a field of view that is approximately 60° of a visual area below and around the applicator;
- at least one high resolution camera, and
- a reflectance modifying agent reservoir.

2. The applicator of claim 1 further comprising a floating ring comprising a plurality of raised contact points.

3. The applicator of claim 1 wherein the telemetric field lens further comprises an LED assembly.

4. The applicator of claim 1 wherein the plurality of wide-angle cameras further comprises at least six miniature wide-angle cameras.

5. The applicator of claim 1 further comprising at least one accelerometer.

6. A method of scanning a region of skin, the method comprising providing a device comprising
- a plurality of wide-angle cameras, and
- a high resolution camera;

moving the device over the region of skin;

capturing a first set of images with the high resolution camera;

capturing a second set of images with the wide-angle cameras;

identifying large features from the second set of images;

identifying small features from the first set of images;

tracking the position of the device relative to the large features and the small features;

creating a map of the large and small features;

calculating cosmetic enhancements within the region of skin;

determining the position of the applicator relative to the small features and large features; and selectively applying a reflectance modifying agent within the region of skin.

7. The method of claim 6 wherein identifying large features further comprises using software to analyze the images captured with one or more wide-angle cameras based on a generic map of large human features.

8. The method of claim 6 further comprising generating a map at a first time; and revising the map at a second time.

9. The method of claim 6 further comprising creating the map based on a skeletal model.

10. The method of claim 6 further comprising using at least one accelerometer to track movements of the device.

11. The method of claim 6 wherein identifying small features from the first set of images further comprises identifying small features selected from the group consisting of pores, moles, scars, lines, wrinkles, age spots, sun damage, freckles, color variations, contours of features, and textural variations such as bumps.

12. The method of claim 6 further comprising
saving the global maps as pix-rich files comprising pixel-level reflectance and topographical data.

13. The method of claim 6 further comprising
manipulating the pix-rich files.

14. The method of claim 6 wherein manipulating the pix-rich files further comprises
using the pix-rich files for gaming or animation.

15. The method of claim 6 wherein manipulating the pix-rich files further comprises
cosmetically enhancing images.

16. The method of claim 6 wherein moving the device over a portion of the body further comprises
moving the device over a portion of the body in multiple passes.

17. The method of claim 6 further comprising
storing the map; and
using the map to correlate the location of the device and landmarks on the skin.

* * * * *